United States Patent [19]

Todoko et al.

[11] Patent Number: 5,202,217

[45] Date of Patent: Apr. 13, 1993

[54] SOLUBILIZATION-INHIBITOR AND POSITIVE RESIST COMPOSITION

[75] Inventors: Masaaki Todoko, Fujisawa; Takashi Taniguchi, Machida; Toru Seita, Atsugi; Shinji Sato, Machida; Katuya Shibata, Higashimurayama, all of Japan

[73] Assignee: Tosoh Corporation, Shinnanyo, Japan

[21] Appl. No.: 562,655

[22] Filed: Aug. 3, 1990

[30] Foreign Application Priority Data

Aug. 8, 1989 [JP] Japan ................... 1-203856
Sep. 22, 1989 [JP] Japan ................... 1-245306
Jan. 23, 1990 [JP] Japan ................... 2-11702
Feb. 9, 1990 [JP] Japan ................... 2-28566

[51] Int. Cl.⁵ .............................. G03C 1/52
[52] U.S. Cl. ...................... 430/191; 430/192; 430/193; 430/270; 430/914
[58] Field of Search ............ 430/191, 189, 192, 193, 430/914, 270

[56] References Cited

U.S. PATENT DOCUMENTS

| | | | |
|---|---|---|---|
| 4,506,006 | 3/1985 | Ruckert | 430/192 |
| 4,696,891 | 9/1987 | Guzzi | 430/191 |
| 4,792,516 | 12/1988 | Toriumi et al. | 430/192 |
| 4,816,380 | 3/1989 | Covington et al. | 430/193 |
| 4,996,301 | 2/1991 | Wilharm et al. | 430/189 |

FOREIGN PATENT DOCUMENTS 0141400 5/1985 European Pat. Off.
0323427 7/1989 European Pat. Off.

OTHER PUBLICATIONS

*Solid State Technology*, vol. 24, No. 8, Aug. 1981, Washington US pp. 81–85; Chandross E. A. et al. "Photoresists for Deep UV Lith . . . ".

*Primary Examiner*—Charles L. Bowers, Jr.
*Assistant Examiner*—Mark F. Huff
*Attorney, Agent, or Firm*—Oblon, Spivak, McClelland, Maier & Neustadt

[57] ABSTRACT

A positive resist composition comprising an aromatic group-containing alkali-soluble resin and a compound having an ammonium salt as skeleton, as the main components.

7 Claims, No Drawings

SOLUBILIZATION-INHIBITOR AND POSITIVE RESIST COMPOSITION

The present invention relates to a positive resist composition. More particularly, it relates to a positive resist for fine working with excellent resolution, which is useful for the production of semiconductor devices such as IC and LSI.

Heretofore, for a positive resist composition composed of a mixture of an alkali-soluble resin (i.e. a resin soluble in an aqueous alkaline solution) and a photosensitive agent, it has been common to use e.g. a novolak resin or a polyvinyl phenol as the alkali-soluble resin, and e.g. an aromatic polyhydroxy compound such as naphthoquinone-(1,2)-diazidosulfonic acid ester as the photosensitive component. As the novolak resin, a phenol-formaldehyde novolak resin or a cresolformaldehyde novolak resin has been widely practically used.

Such a positive photoresist composition is designed so that when irradiated with active radiation, a quinonediazide compound contained in the composition is converted to indene carboxylic acid and becomes soluble in an aqueous alkaline solution, and utilizing this nature, a positive pattern is formed by subsequent development with an alkaline solution. For this purpose, it has been common to employ a reduction-type projection printing using a light of g-line (436 nm) or i-line (365 nm). However, with the lithography technique using such ultraviolet rays, the maximum resolution is expected to be about from 0.5 to 0.6 $\mu$m, and it is believed to be difficult by a conventional lithography technique to resolve a line width of less than 0.5 $\mu$m required for the production of 64M DRAM. Under these circumstances, an attention has been drawn to a deep ultraviolet lithography technique in which a light of a shorter wavelength is used, and recently, there have been active movements for development of a reduction-type projection printing method using a KrF excimer laser (249 nm). The shorter the wavelength of the light used, the higher the resolution becomes, but there will be a serious problem with respect to the resist material. For example, in the novolak resist used for the ultraviolet lithography (a composition comprising a novolak resin and a naphthoquinone-(1,2)-diazidosulfonic acid ester), the base polymer contains an aromatic ring, and therefore absorption of far ultraviolet rays is substantial, and the light transmittance is at a level of 20%. Further, the naphthoquinone-(1,2)-diazidosulfonic acid ester as a photosensitive solubilization inhibitor, also contains an aromatic ring. Therefore, bleaching will not take place at the far ultraviolet region, and the light for exposure hardly reaches the bottom of the resist. Even if KrF excimer laser stepper exposure is conducted, no satisfactory pattern will be obtained. On the other hand, with a PMMA resist excellent in the light transmittance, the sensitivity is low and the dry etching resistance is poor, although a good pattern can be obtained. Thus, as a resist for far ultraviolet rays, there has been found no material which is excellent in all of the sensitivity, the resolution and the dry etching resistance.

As described in the foregoing, with a solubilization-inhibiting type resist for far ultraviolet rays, the transparency and bleaching properties of the solubilization-inhibitor give a substantial influence over the resist performance, particularly the resolution. Therefore, it is desired to develop a solubilization-inhibitor excellent in the transparency and the bleaching properties. On the other hand, with respect to the alkali-soluble resin constituting the base polymer, a highly transparent resin such as polyvinyl phenol is available, and the research for the resists is directed primarily to the development of the photosensitive agent.

Further, in recent years, an o-nitrobenzyl ester of cholic acid (E. Reichmanis, et al., J. Vac. Sui. Technol., 19, 1338 (1981)) and 5-diazomeldramic acid (B. D. Grant, et al., IEEE Trans. Electron Devices, ED-28, 1300 (1981)) have been studied as solubilization-inhibitors for far ultraviolet rays. However, the former contains an aromatic ring and thus is poor in the bleaching properties, and its solubilization-inhibiting ability is not high. The latter has high bleaching properties but has problems that the solubilization-inhibiting ability is small, and it has a sublimation property.

As described in the foregoing, the conventional solubilization-inhibitors are poor in the light transmittance of far ultraviolet rays, and those having good bleaching properties are poor in the solubilization-inhibiting performance, whereby the film remaining rate is low. Therefore, they are not practically useful for far ultraviolet rays.

It is an object of the present invention to provide a photosensitive agent system having high transparency to far ultraviolet rays and having a high solubilization-inhibiting performance, and a resist using such a photosensitive agent.

Under these circumstances, the present inventors have conducted extensive studies and as a result, have found that a compound having an ammonium salt as skeleton has a high level of solubilization-inhibiting ability against an alkali-soluble resin, and it also will make a photosensitive agent excellent in light transmittance. The present invention has been accomplished on the basis of these discoveries.

Thus, the present invention provides a positive resist composition comprising an aromatic group-containing alkali-soluble resin and a compound having an ammonium salt as skeleton, as the main components.

More specifically, the present invention provides a positive resist composition containing an ammonium salt as a component, which ammonium salt contains at least one group being possible to give a carboxylic acid group or phenolic group by the action of Bronsted or Lewis acid, or light. The ammonium salt is represented by one of the following formulas (1) to (4):

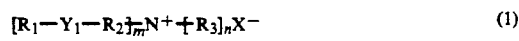
$$[R_1-Y_1-R_2\!\!+\!\!_m N^+ + R_3]_n X^- \qquad (1)$$

wherein each of $R_1$ and $R_2$ which may be the same or different, is a chain alkyl group having from 1 to 30 carbon atoms, a polycyclic alkyl group, a chain alkoxy group, a polycyclic alkoxy group or an allyl group, $R_3$ is a chain alkyl group having from 1 to 30 carbon atoms, a polycyclic alkyl group or an allyl group, $X^-$ is a halogen$^-$, $HSO_4^-$, $ClO_4^-$ or $BF_4^-$, $Y_1$ is an acid-decomposable group, m is an integer of at least 1 and n is an integer inclusive of 0, provided that $m+n=4$;

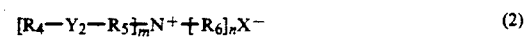
$$[R_4-Y_2-R_5\!\!+\!\!_m N^+ + R_6]_n X^- \qquad (2)$$

wherein each of $R_4$ and $R_5$ which may be the same or different, is a chain alkyl group having from 1 to 30 carbon atoms, a polycyclic alkyl group, a chain alkoxy group, a polycyclic alkoxy group or an allyl group, $R_6$ is a hydrogen atom, a chain alkyl group having from 1 to 30 carbon atoms, a polycyclic alkyl group or an allyl group, $X^-$ is a halogen$^-$, $HSO_4^-$, $ClO_4^-$ or $BF_4^-$, $Y_2$ is a radiation-decomposable group of the formula:

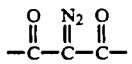

is an integer of at least 1, and n is an integer inclusive of 0, provided that $m+n=4$;

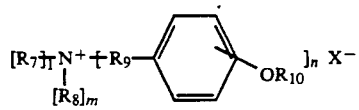

wherein each of $R_7$, $R_8$ and $R_9$ which may be the same or different, is a chain alkyl group having from 1 to 30 carbon atoms, a polycyclic alkyl group, a chain alkoxy group, a polycyclic alkoxy group or an allyl group, $R_{10}$ is

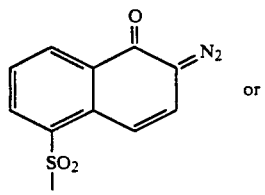

or

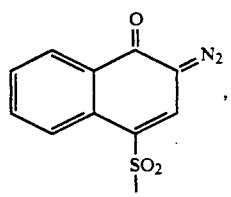

$X^-$ is a halogen$^-$, $HSO_4^-$, $ClO_4^-$ or $BF_4^-$, each of l and m is an integer inclusive of 0, and n is an integer of at least 1, provided that $l+m+n=4$; and

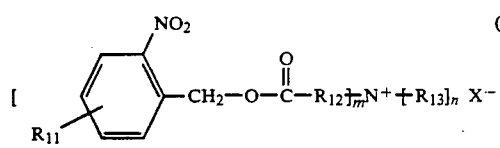

wherein $R_{11}$ is a hydrogen atom, a chain alkyl group having from 1 to 30 carbon atoms, a polycyclic alkyl group or a nitro group, $R_{12}$ is a chain alkyl group having from 1 to 30 carbon atoms, a polycyclic alkyl group or an allyl group, $R_{13}$ is a chain alkyl group having from 1 to 30 carbon atoms, a polycyclic alkyl group or an allyl group, $X^-$ is a halogen$^-$, $HSO_4^-$, $ClO_4^-$ or $BF_4^-$, m is an integer of at least 1, and n is an integer inclusive of 0, provided that $m+n=4$.

Now, the positive resist composition of the present invention will be described in further detail.

The present inventors have studied various compounds for their solubilization-inhibiting abilities against an alkali-soluble resin such as polyvinyl phenol, and as a result, have found that an alkyl ammonium salt has a high solubilization-inhibiting ability. The solubilization-inhibiting ability of an alkyl ammonium salt depends largely on the structure of the salt. Namely, the longer the chain of the alkyl group, i.e. the larger the carbon number, the higher the solubilization-inhibiting ability, and the larger the number of long chain alkyl groups, the higher the solubilization-inhibiting ability. Namely, it has been found that there is a substantial difference in the solubilization-inhibiting ability between a tetra long chain alkyl ammonium salt and a tetra short chain alkyl ammonium salt. Further, it has been found also that there is a remarkable difference in the solubilization-inhibiting ability between a case where a carboxyl group or a phenol group is contained in the ammonium salt and a case where no such a group is contained. Namely, when a carboxyl group or a phenol group is contained in the ammonium salt, no substantial solubilization-inhibiting ability is shown. Accordingly, by employing a compound containing an alkyl ammonium salt and a group capable of forming a carboxyl group or a phenol group by the decomposition under irradiation with active radiation, or a group capable of forming a carboxyl group or a phenol group by the decomposition with an acid formed under irradiation with active radiation, simultaneously, it is possible to control the solubilization-inhibiting ability by the chain length of the alkyl group. Further, by the exposure, the carboxyl group or a phenol group will be formed and the chain length becomes short, whereby the exposed portion will have improved solubility to the alkaline developing solution, whereas the non-exposed portion will have no change in the solubility, and patterning will thereby be possible. Such properties are not limited to far ultraviolet ray exposure, and so long as a carboxyl group or a phenol group will be formed, or the chain length will be shortened under irradiation with ultraviolet rays, electron rays or X-rays, such a material may be used as a resist for the corresponding radiation.

As the acid-decomposable group ($Y_1$) in the formula (1), an ester group, a carbonate group, a silyl ether or a silyl ester group may be mentioned. As ammonium salts containing such acid-decomposable groups, salts of the following formulas (5), (6), (7) and (8) may, for example, be mentioned.

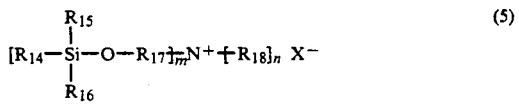

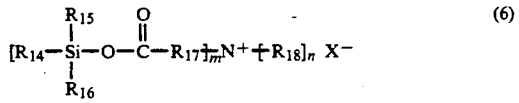

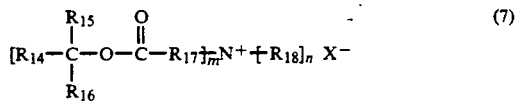

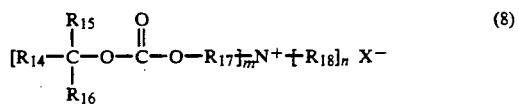

In the above formulas, each of $R_{14}$, $R_{15}$ and $R_{16}$ which may be the same or different, is a hydrogen atom, a chain alkyl group having from 1 to 30 carbon atoms, a polycyclic alkyl group, a chain alkoxy group, a polycyclic alkoxy group or an allyl group. $R_{17}$ is a chain alkyl group having from 1 to 30 carbon atoms, a polycyclic alkyl group, a chain alkoxy group, a polycyclic alkoxy group or an allyl group, $R_{18}$ is a chain alkyl group having from 1 to 30 carbon atoms, a polycyclic alkyl group or an allyl group, $X^-$ is a halogen$^-$, $HSO_4^-$, $ClO_4^-$ or $BF_4^-$, m is an integer of at least 1, and n is an integer inclusive of 0, provided that $m+n=b$ 4.

Specifically, the following compounds may be mentioned:

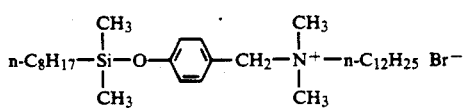

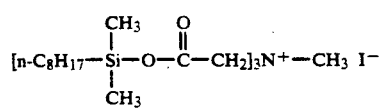

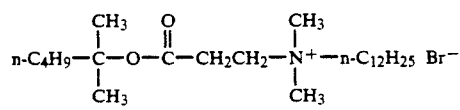

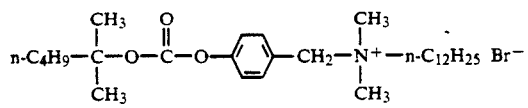

However, the acid-decomposable group is not restricted to the above so long as it is capable of being decomposed by an acid.

The acid-forming agent used for the above ammonium salt is the one which generates an acid when irradiated with active radiation such as ultraviolet rays, far ultraviolet rays, excimer lasers or electron beams. Number of compounds are known as such acid-forming.

Examples of such compounds include a halogenated diphenyl ethane derivative of the following formula (9), a sulfonic acid ester derivative of the following formula (10), an iodonium salt of the following formula (11), and a sulfonium salt of the following formula (12):

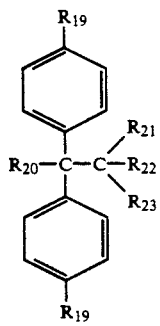
(9)

$R_{24}-O-SO_2-R_{25}$ (10)

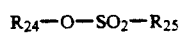
(11)

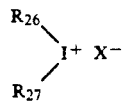

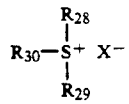
(12)

The halogenated diphenyl ethane derivative of the formula (9) is the one capable of forming a halogenoacid when irradiated with active radiation. In the formula, $R_{19}$ is a hydrogen atom, a halogen atom, an alkyl group, an alkoxy group, a hydroxyl group or a nitro group, $R_{20}$ is a hydrogen atom, a hydroxyl group or $R_{31}-CONH-$ (wherein $R_{31}$ is an alkyl group), $R_{21}$ is a halogen atom, and each of $R_{22}$ and $R_{23}$ is a hydrogen atom, a halogen atom or an alkyl group.

The sulfonic acid ester derivative of the above formula (10) is the one capable of forming a sulfonic acid when irradiated with active radiation. In the formula, $R_{24}$ is a group blocking the hydrogen site of sulfonic acid. Such a group includes:

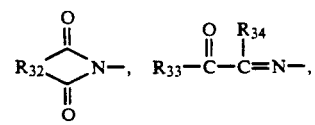

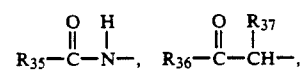

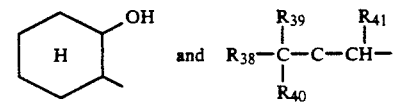

wherein $R_{32}$ is an alkylene group, an alkenylene group or an arylene group, each of $R_{33}$, $R_{34}$, $R_{35}$, $R_{37}$ and $R_{41}$ is an alkyl group or an aryl group, each of $R_{36}$ and $R_{38}$ is an aryl group, and each of $R_{39}$ and $R_{40}$ is a hydrogen atom, an alkyl group or an aryl group. Further, $R_{25}$ is an alkyl group or an allyl group.

The iodonium salt of the above formula (11) and the sulfonium salt of the above formula (12) are the ones capable of forming Lewis acids when irradiated with active radiation. In the formulas, each of $R_{26}$, $R_{27}$, $R_{28}$ and $R_{29}$ is an aryl group, $R_{30}$ is an alkyl group or an aryl group, and $X^-$ is $BF_4^-$, $PF_6^-$, $AsF_6^-$, $SbF_6^-$ or $ClO_4^-$.

Specific examples of such an acid-forming agent include:

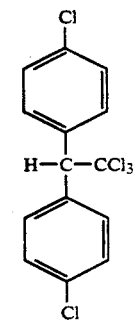
(9-1)

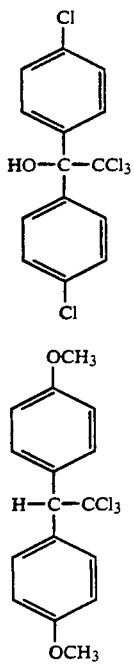

(9-2)

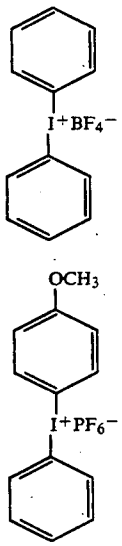

(11-1)

(9-3)

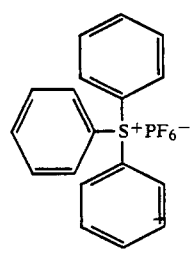

(11-2)

(10-1)

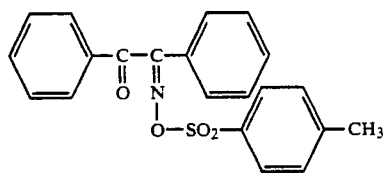

(12-1)

(10-2)

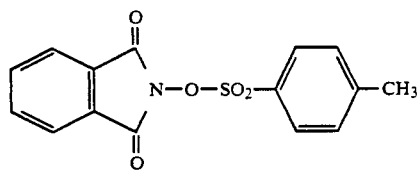

(12-2)

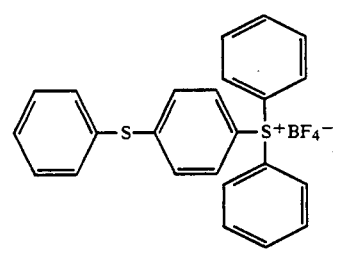

(10-3)

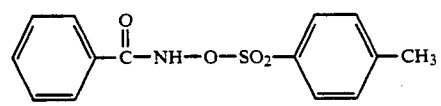

However, the acid-forming agent is not limited to those exemplified above. Further, naphthoquinone-(1,2)-diazidosulfonic acid esters and diazomeldramic acid, o-nitrobenzyl esters which are used as photosensitive agents for positive photoresists, may also be employed. Such acid-forming agents by radiation may be used alone or in combination as a mixture of two or more.

(10-4)

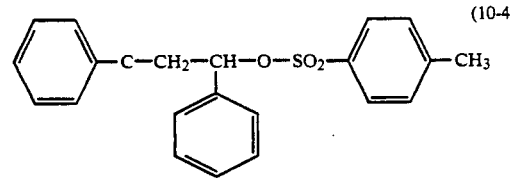

(10-5)

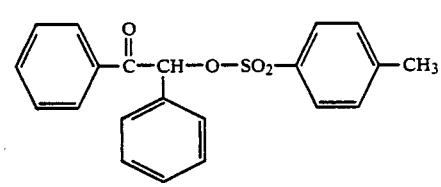

In a case where an ammonium salt having such an acid-decomposable group is employed, the proportions of the respective components are such that the ammonium salt is from 1 to 40 parts by weight relative to 100 parts by weight of the alkali-soluble resin, and the acid-forming agent by radiation is from 0.1 to 50 parts by weight relative to 100 parts by weight of the ammonium salt.

(10-6)

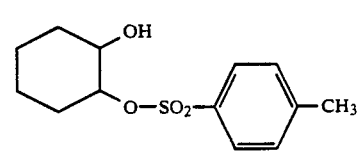

If the proportion of the acid-forming agent by radiation is small, the acid concentration will be low, and the decomposition will not adequately proceed, whereby no adequate difference in the solubility will be obtained as between the exposed portion and the non-exposed portion. On the other hand, if the proportion of the acid-forming agent by radiation is large, the light transmittance of the resist film decreases, whereby it will be difficult to obtain a pattern having good contrast. Further, in order to facilitate the decomposition by an acid, heat treatment may be applied after the exposure.

The proportion of the ammonium salt to the alkali-soluble resin, is from 1 to 40 parts by weight relative to 100 parts by weight of the alkali-soluble resin. If the proportion is less than 1 part by weight, no adequate solubilization-inhibiting performance will be obtained. On the other hand, if the proportion exceeds 40 parts by weight, there will be adverse effects to the coating properties of the resist film or to the dry etching resistance.

The compound of the formula (2) includes the following specific examples:

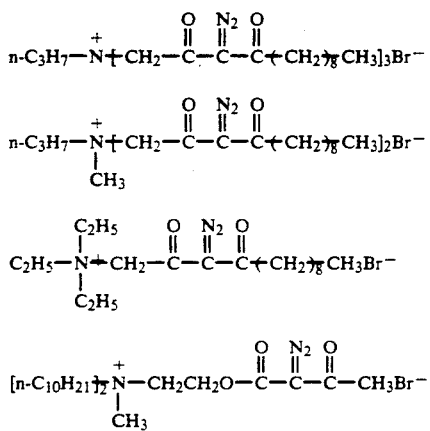

However, the compound of the formula (2) is not limited to the above structures.

These ammonium salts undergo bleaching upon exposure, and the light transmittance after bleaching becomes so high that the radiation reaches the bottom of the resist.

The proportion of the ammonium salt containing such a radiation-decomposable group to the alkali-soluble resin is usually from 1 to 40 parts by weight, preferably from 2 to 30 parts by weight, relative to 100 parts by weight of the alkali-soluble resin. If the proportion is less than 1 part by weight, no adequate solubilization-inhibiting ability will be obtained. On the other hand, if it exceeds 40 parts by weight, there will be adverse effects to the coating properties of the resist film or to the dry etching resistance.

The compound of the formula (3) includes the following specific examples:

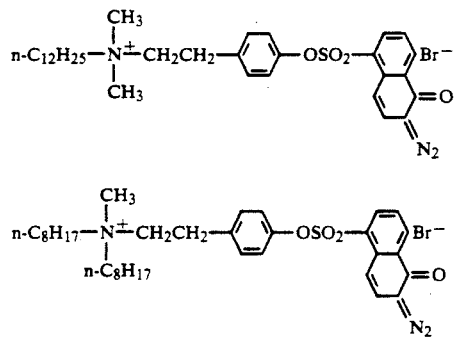

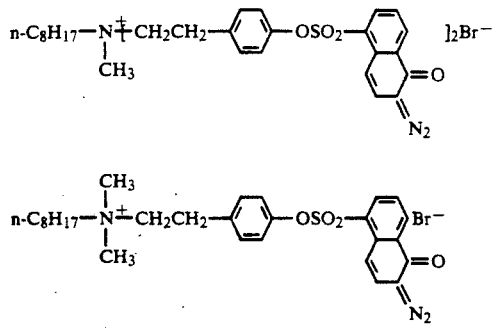

However, the compound of the formula (3) is not limited to the above structures.

Such ammonium salts containing a naphthoquinone diazido group have a high solubilization-inhibiting ability, and their contents in the resist compositions can thereby be reduced as compared with the conventional naphthoquinone diazido compounds. Further, they contain no benzophenone moiety, and the light transmittance of the photosensitive agent itself is improved. Accordingly, they can be used for the preparation of resist compositions for ultraviolet rays and far ultraviolet rays having high sensitivity and high resolution.

The proportion of the ammonium salt having such a naphthoquinone azido group to the alkali-soluble resin is usually from 1 to 30 parts by weight, preferably from 5 to 20 parts by weight, relative to 100 parts by weight of the alkali-soluble resin. If the proportion is less than 1 part by weight, no adequate solubilization-inhibiting ability can be obtained. On the other hand, if it exceeds 30 parts by weight, there will be adverse effects to the coating properties of the resist film or to the dry etching resistance.

The compound of the formula (4) includes the following specific examples:

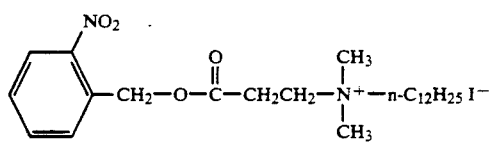

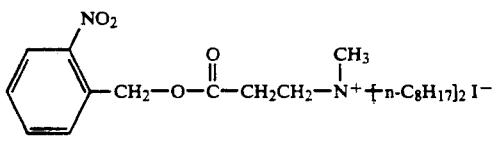

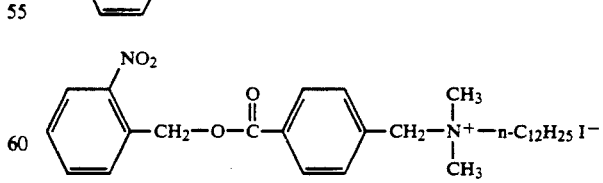

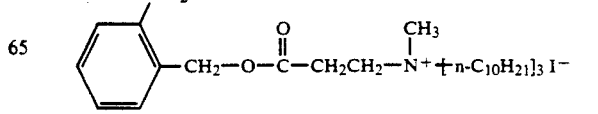

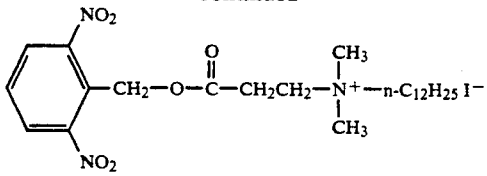

However, the compound of the formula (4) is not limited to the above structures.

These ammonium salts have high solubilization-inhibiting ability, and their content in the resist compositions can be reduced, and the transparency of the resist film will be high.

The proportion of such an ammonium salt containing an o-nitrobenzyl ester group to the alkali-soluble resin is usually from 1 to 40 parts by weight, preferably from 2 to 30 parts by weight, relative to 100 parts by weight of the alkali-soluble resin. If the proportion is less than 1 part by weight, no adequate solubilization-inhibiting ability will be obtained, and if it exceeds 30 parts by weight, there will be adverse effects to the coating properties of the resist film or to the dry etching resistance.

The alkali-soluble resin useful for the present invention includes a phenol-formaldehyde novolak resin, a cresol-formaldehyde novolak resin, a polyhydroxylene, a copolymer of a hydroxystyrene monomer with other vinyl monomer, a copolymer of a methacrylic acid monomer with other aromatic group-containing vinyl monomer such as a styrene-methacrylic acid copolymer, a copolymer of a methyl methacrylic acid monomer with other aromatic group-containing vinyl monomer, such as a styrene-methacrylic acid copolymer, and a resin containing a phenol group or a carboxyl group and an aromatic group. However, the alkali-soluble resin of the present invention is not limited to such specific examples.

The resist composition of the present invention is soluble in an organic solvent. When it is used for the preparation of integrated circuits, it is employed usually in the form of a solution (a resist solution). In such a case, the above composition is dissolved usually in an amount of from 1 to 50% by weight, preferably from 5 to 30% by weight, in an organic solvent and adjusted. The solvent to be used for this purpose is preferably the one which is capable of uniformly dissolving the respective components of the positive photoresist composition of the present invention and capable of providing a uniform smooth coating layer when the solution is applied to the surface of a substrate such as silicon or aluminum, followed by evaporation of the organic solvent. Specifically, it includes a ketone solvent such as acetone, methyl ethyl ketone, cyclopentanone or cyclohexanone, a cellosolve solvent such as methyl cellosolve, ethyl cellosolve, butyl cellosolve, methyl cellosolve acetate or ethyl cellosolve acetate, and ether solvent such as tetrahydrofuran or diethylene glycol dimethyl ether, and an ester solvent such as ethyl acetate or butyl acetate. However, the solvent is not limited to such specific examples.

The above organic solvents may be used alone or in combination as a mixture of two or more.

In addition to the above components, sensitizers, dyes, plasticizers, other resins, inhibitors such as thermal reaction inhibitors and adhesion promotors, may be added to the resist compositions of the present invention, as the case requires.

As mentioned above, the positive resist composition of the present invention may be prepared into a resist solution, and a relief pattern may be formed with it by means of conventional photoresist techniques.

Now, the method of forming such a relief pattern will be described.

Firstly, the resist solution prepared as described above, is coated on a substrate. The coating of the substrate may be conducted by e.g.e a spinner. Then, the coated solution is subjected to baking at a temperature of from 60° to 120° C., preferably from 80° to 100° C., for from 20 to 60 minutes. After baking, ultraviolet rays, for ultraviolet rays or excimer laser is irradiated to this coating film through a photomask chart. Middle ultraviolet rays may also be employed.

If necessary, the substrate is then subjected to heat treatment at a temperature of not higher than 160° C. by means of e.g. a hot plate.

Then, the exposed portions will be washed away with a developing solution to obtain a relief pattern. As the developing solution, a weakly alkaline aqueous solution having a concentration of e.g. not higher than 5% by weight of e.g. sodium hydroxide, potassium hydroxide, sodium metasilicate of tetramethylammonium hydroxide, may be employed. The resist pattern thus formed is excellent in both resolution and contrast.

Further, by using the pattern formed by using the resist composition of the present invention as described above, as a mask, it is possible to conduct etching of a substrate.

Now, the present invention will be described in further detail with reference to Examples. However, it should be understood that the present invention is by no means restricted by such specific Examples.

PREPARATION EXAMPLE 1

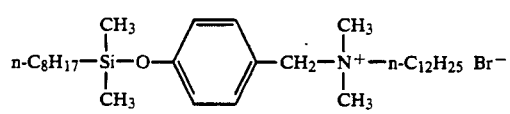

1.1 Preparation of

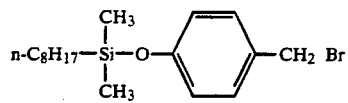

Into a 100 ml three-necked flask equipped with a reflux condenser, a dropping funnel and a stirrer, 10 g (54 mmol) of 4-hydroxybenzyl bromide, 9.1 g (134 mmol) of imidazole and 10 ml of dry dimethylformamide (DMF) were introduced and stirred. Then, 13.3 g (64 mmol) of n-octyldimethylchlorosilane was dropwise added over a period of 10 minutes, and the mixture was stirred at room temperature for 24 hours. After completion of the reaction, the solvent was distilled off under reduced pressure, and 50 ml of chloroform was added to the residue. The mixture was washed three times with 50 ml of a 0.1N sodium chloride aqueous solution. The chloroform solution was concentrated under reduced pressure and then dried under vacuum to obtain the above identified compound.

Amount 15.3 g, Yield: 81%.

1.2 Preparation of

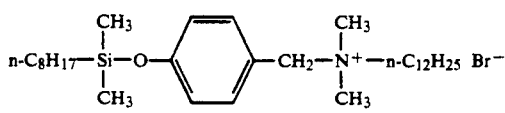

Into a 50 mol three-necked flask equipped with a reflux condenser and a stirrer, 3.58 g of N,N-dimethyl-n-dodecylamine and 0.5 ml of dry ethanol were added and stirred. Then, 5.0 g (14 mmol) of the compound obtained in step 1.1 was dropwise added over a period of 30 minutes, and the mixture was heated and refluxed. After completion of the reaction, the reaction mixture was poured into 100 ml of ethyl ether. The precipitates formed were separated, then washed with 10 ml of ethyl ether and dried under vacuum to obtain the above identified compound.

Amount; 4.4 g, Yield: 55%.

Characteristic peak in the $^1$H-NMR spectrum (CDCl$_3$):

A ($\delta$0.07 —O—Si(CH$_3$)$_2$—)
B ($\delta$3.3 =N$^+$ —(CH$_3$)$_2$)
C ($\delta$0.84 terminal methyl)
Intensity ratio of A:B:C = 1:1:1

PREPARATION EXAMPLE 2

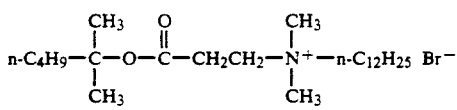

2.1 Preparation of

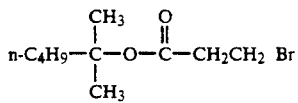

Into a 100 ml three-necked flask equipped with a reflux condenser, a dropping funnel and a stirrer, 10 g (86.1 mmol) of 2-methyl-2-hexanol and 50 ml of dry pyridine were introduced and stirred. Then, 17.7 g (103.3 mmol) of 3-bromopropionyl chloride was dropwise added over a period of 30 minutes under cooling in an ice water bath, and the mixture was stirred at room temperature for 24 hours. After completion of the reaction, the solvent was distilled off under reduced pressure, and the above identified compound was isolated by silica gel column chromatography.

Amount: 16.2 g, Yield: 75%.

2.2 Preparation of

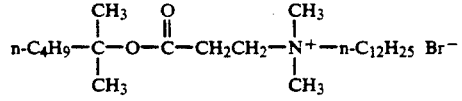

Into a 50 ml three-necked flask equipped with a reflux condenser and a stirrer, 4.0 g (22.5 mmol) of N,N-dimethyl-n-dodecylamine and 5.0 ml of dry ethanol were introduced and stirred. Then, 5.6 g (22.5 mmol) of the compound obtained in step 2.1 was dropwise added over a period of 30 minutes, and the mixture was heated and refluxed. After completion of the reaction, the reaction mixture was poured into 100 ml of ethyl ether. The precipitate formed were separated, then washed with 10 ml of ethyl ether and dried under vacuum to obtain the above identified compound.

Amount: 5.2 g, Yield: 65%.

Characteristic peaks in the $^1$H-NMR spectrum (CDCl$_3$):

A ($\delta$0.07 —O—Si(CH$_3$)$_2$—)
B ($\delta$3.3 =N$^+$ —(CH$_3$)$_2$)
C ($\delta$0.84 terminal methyl)
Intensity ratio of A:B:C = 1:1:1.

EXAMPLE 1

A resist composition having the following composition was prepared.

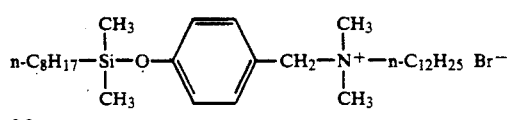

0.3 g

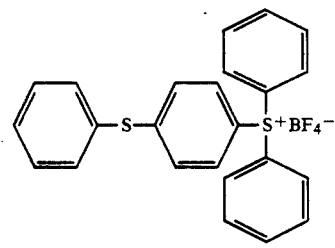

0.03 g

This resist solution was spin-coated at a rate of 2,500 rpm/60 sec on a silicon wafer having hexamethyldisilazane (HMDS) spin-coated thereon at a rate of 2,000 rpm/60 sec. This wafer was prebaked in an oven at 80° C. for 30 minutes to obtain a coating film of 1.0 μm. Then, the above coating film was subjected to exposure at various doses by means of a KrF excimer laser stepper (NA=0.35). Then, the wafer was heat-treated at 100° C. for 90 seconds on a hot plate and then developed with a 2.38% tetramethylammonium hydroxide aqueous solution for 1 minute, then rinsed with water for 1 minute, whereupon the thickness of the remaining resist film was measured. Then, the remaining film thickness (standardized) was plotted against the dose for exposure (mj/cm$^2$), and the minimum dose (sensitivity) where the remaining film thickness became 0, was determined and found to be about 35 mj/cm$^2$. Thus, it was found to be a positive resist of high sensitivity. Then, the resist film obtained in the same manner as above was subjected to exposure (50 mj/cm$^2$) using a quartz mask, followed by development under the same condition as above, whereby a L & S pattern of 0.5 μm with an excellent profile was obtained.

EXAMPLE 2

The operation was conducted in the same manner as in Example 1 except that the following compound was used as the ammonium salt:

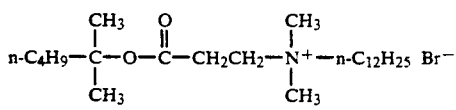

A sensitivity of 50 mj/cm$^2$ was obtained, and a L & S pattern of 0.5 μm with an excellent profile was obtained.

EXAMPLE 3

The operation was conducted in the same manner as in Example 1 except that the following compound was used as the acid-forming agent:

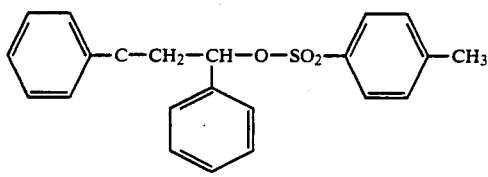

A sensitivity of 90 mj/cm$^2$ was obtained, and a L & S pattern of 0.5 μm with an excellent profile was obtained.

EXAMPLE 4

The operation was conducted in the same manner as in Example 1 except that an electron beam exposure apparatus (accelerating voltage of 20 kV) was used instead of the KrF excimer laser stepper (NA=0.35). As a result, a sensitivity of 15 μC/cm$^2$ was obtained, and a L & S pattern of 0.5 μm with an excellent profile was obtained.

EXAMPLE 5

The operation was conducted in the same manner as in Example 2 except that an electron beam exposure apparatus (accelerating voltage of 20 kV) was used instead of the KrF excimer laser stepper (NA=0.35). As a result, a sensitivity of 20 μC/cm$^2$ was obtained, and a L & S pattern of 0.5 μm with an excellent profile was obtained.

EXAMPLE 6

The operation was conducted in the same manner as in Example 3 except that an electron beam exposure apparatus (accelerating voltage of 20 kV) was used instead of KrF excimer laser stepper (NA=0.35). As a result, a sensitivity of 12 μC/cm$^2$ was obtained, and a L & S pattern of 0.5 μm with an excellent profile was obtained.

PREPARATION EXAMPLE 3

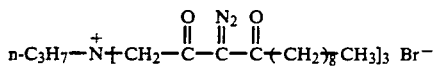

3.1 Preparation of

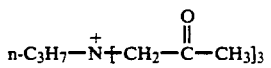

Into a 100 ml three-necked flask equipped with a reflux condenser, a dropping funnel and a stirrer, 10 g (169 mmol) of n-propylamine and 50 ml of ethyl ether were introduced and stirred. Then, 11.59 g (84.6 mmol) of bromoacetone was dropwise added over a period of 10 minutes, and the mixture was heated and refluxed for 24 hours. After completion of the reaction, the solvent was distilled off under reduced pressure, and n-propylamino acetone was isolated by silica gel column chromatography.

Amount: 4.58 g, Yield: 47%.

Into a 100 ml three-necked flask equipped with a reflux condenser, a dropping funnel and a stirrer, 4.58 g (39.8 mmol) of n-propylaminoacetone and 20 ml of ethyl ether were introduced and stirred. Then, 2.72 g (19.9 mmol) of bromoacetone was dropwise added over a period of 10 minutes, and the mixture was heated and refluxed for 24 hours. After completion of the reaction, the solvent was distilled off under reduced pressure, and n-propylaminodiacetone was isolated by silica gel column chromatography.

Amount: 1.36 g, Yield: 40%.

Into a 50 ml three-necked flask equipped with a reflux condenser and a stirrer, 1.36 g (7.94 mmol) of n-propylaminodiacetone, 1.25 g (9.13 mmol) of bromoacetone and 5 ml of ethanol were introduced, and heated and refluxed for 24 hours. After completion of the reaction, the reaction solution was poured into 30 ml of ethyl ether. The precipitates formed was separated, then washed with 5 ml of ethyl ether and dried to obtain the above identified compound.

Amount: 1.71 g, Yield: 70%.

3.2 Preparation of

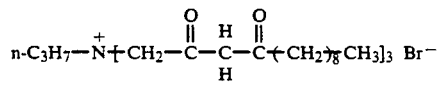

Into a 50 ml three-necked flask equipped with a reflux condenser, a dropping funnel and a stirrer, 1.71 g (5.55 mmol) of the compound obtained in step 3.1, 0.80 g (33.3 mmol) of sodium hydride, 5 ml of ethyl ether and 5 ml of DMF were introduced, heated and refluxed. Then, 6.66 g (33.3 mmol) of ethyl n-caprate was dropwise added under stirring, and the mixture was then heated and refluxed for 1 hour. After completion of the reaction, the reaction solution was poured into 30 ml of ethyl ether. The precipitates formed were separated, then washed with 5 ml of ethyl ether and dried to obtain the above identified compound.

Amount: 3.42 g, Yield: 80%.

3.3 Preparation of

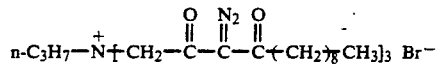

Into a 50 ml three-necked flask equipped with a reflux condenser and a stirrer, 3.42 g (4.44 mmol) of the compound obtained in item 3.2, 1.48 g (14.6 mmol) of triethylamine, 10 ml of acetonitrile and 15 ml of DMF were introduced, and 5 ml of an acetonitrile solution containing 2.87 g (14.6 mmol) of p-toluenesulfonylazide, was dropwise added thereto. The mixture was stirred at room temperature for 3 hours and then concentrated under reduced pressure. The concentrated solution was poured into 30 ml of ethyl ether. The precipitates formed were separated, then washed with 5 ml of ethyl ether and dried to obtain the above identified compound.

Amount: 3.01 g, Yield: 80%.

Characteristic peaks in the IR spectrum: 2,150 cm$^{-1}$.

Elemental Analysis

C=61.2% (calculated: 59.4%)
H=8.5% (calculated: 8.3%)
N=10.3% (calculated: 11.5%)

PREPARATION EXAMPLE 4

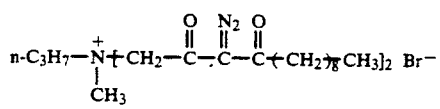

4.1 Preparation of

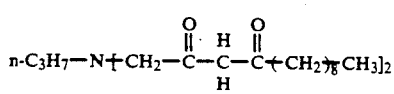

Into a 50 ml three-necked flask equipped with a reflux condenser, a dropping funnel and a stirrer, 1.0 g (5.84 mmol) of the n-propylaminodiacetone compound obtained in step 3.1 of Preparation Example 3, 0.567 g (23.4 mmol) of sodium hydride, 5 ml of ethyl ether and 5 ml of DMF were introduced, and the mixture was heated and refluxed Then, 4.68 g (23.7 mmol) of ethyl n-caprate was dropwise added over a period of 10 minutes under stirring, and then the mixture was heated and refluxed for 1 hour. After completion of the reaction, the solvent was distilled off under reduced pressure, and the above identified compound was isolated by silica gel column chromatography.

Amount: 2.1 g, Yield: 75%.

4.2 Preparation of

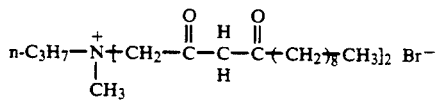

Into a 50 ml three-necked flask equipped with a reflux condenser and a stirrer, 2.1 g (4.38 mmol) of the compound obtained in step 4.1, 0.46 g (4.82 mmol) of bromomethane and 5 ml of ethanol were introduced, and the mixture was heated and refluxed for 24 hours. After completion of the reaction, the reaction solution was poured into 30 ml of ethyl ether. The precipitates formed were separated, then washed with 5 ml of ethyl ether and dried to obtain the above identified compound.

Amount: 2.14 g, Yield: 85%.

4.3 Preparation of

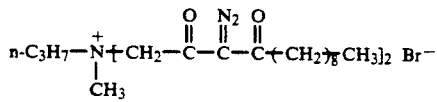

Into a 50 ml three-necked flask equipped with a reflux condenser and a stirrer, 2.14 g (3.72 mmol) of the compound obtained in step 4.2, 0.82 g (8.18 mmol) of triethylamine, 10 ml of acetonitrile and 15 ml of DMF were introduced. Further, 5 ml of an acetonitrile solution containing 1.61 g (8.18 mmol) of t-toluenesulfonylazide, was dropwise added thereto. The mixture was stirred at room temperature for 3 hours and then concentrated under reduced pressure. The concentrated solution was poured into 30 ml of ethyl ether. The precipitates formed were separated, then washed with 5 ml of ethyl ether and dried to obtain the above identified compound.

Amount: 1.86 g, Yield: 80%.

Characteristic peak in the IR spectrum: 2,150 cm$^{-1}$.

Elemental Analysis

C=58.4% (calculated: 57.5%)
H=8.6% (calculated: 8.4%)
N=10.9% (calculated: 11.2%)

PREPARATION EXAMPLE 5

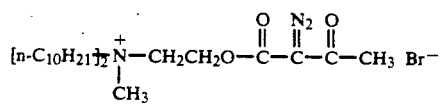

5.1 Preparation of

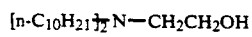

Into a 100 ml three-necked flask equipped with a reflux condenser, a dropping funnel and a stirrer, 10 g (33.6 mmol) of di-n-decylamine and 50 ml of ethyl ether were introduced and stirred. Then, 2.10 g (16.8 mmol) of 2-bromoethanol was dropwise added over a period of 10 minutes, and the mixture was heated and refluxed for 24 hours. After completion of the reaction, the solvent was distilled off under reduced pressure, and the above identified compound was isolated by silica gel column chromatography.

10 Amount: 3.16 g, Yield: 55%.

5.2 Preparation of

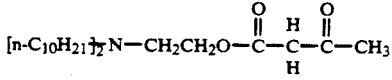

Into a 100 ml three-necked flask equipped with a reflux condenser, a dropping funnel and a stirrer, 3.16 g (9.25 mmol) of the compound obtained in step 5.1, 15 ml of benzene and 0.3 g of sodium acetate were introduced, and the mixture was heated and refluxed. Then, 5 ml of a benzene solution containing 3.11 g (37 mmol) of diketone, was dropwise added over a period of 30 minutes. Then, the mixture was heated and refluxed for 4 hours. After completion of the reaction, the solvent was distilled off under reduced pressure, and the above identified compound was isolated by silica gel column chromatography.

Amount: 2.36 g, Yield: 60%.

5.3 Preparation of

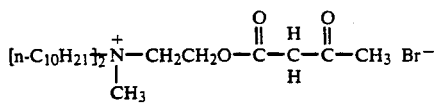

Into a 50 ml three-necked flask equipped with a reflux condenser and a stirrer, 2.36 g (5.54 mmol) of the compound obtained in step 5.2, 0.58 g (6.10 mmol) of bromomethane and 5 ml of ethanol were introduced, and the mixture was heated and refluxed for 24 hours. After completion of the reaction, the reaction solution was poured into 30 ml of ethyl ether. The precipitates formed were separated, then washed with 5 ml of ethyl ether and dried to obtain the above identified compound.

Amount 2.45 g, Yield: 85%.

5.4 Preparation of

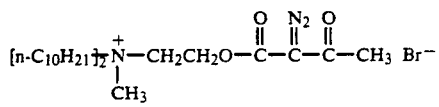

Into a 50 ml three-necked flask equipped with a reflux condenser and a stirrer, 2.45 g (4.70 mmol) of the compound obtained in step 5.3, 0.53 g (5.20 mmol) of triethylamine, 10 ml of acetonitrile and 15 ml of DMF were introduced. Further, 5 ml of an acetonitrile solution containing 1.02 g (5.02 mmol) of p-toluene sulfonyl azide was dropwise added thereto. The mixture was stirred at room temperature for 3 hours, and then concentrated under reduced pressure. The concentrated solution was poured into 30 ml of ethyl ether. The precipitates formed were separated, then washed with 5 ml of ethyl ether and dried to obtain the above identified compound.

Amount: 1.80 g, Yield: 70%.
Characteristic peak in the IR spectrum: 2,150 cm$^{-1}$.

Elemental Analysis

C=60.2% (calculated: 59.3%)
H=9.7% (calculated: 9.59%)
N=7.5% (calculated: 7.69%)

EXAMPLE 7

A resist composition having the following composition was prepared.

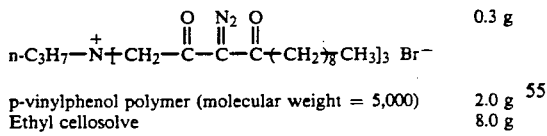  0.3 g p-vinylphenol polymer (molecular weight = 5,000)  2.0 g
Ethyl cellosolve  8.0 g This resist solution was spin-coated at a rate of 2,500 rpm/60 sec on a silicon wafer having hexamethyldisilazan (HNDS) spin coated thereon at a rate of 2,000 rpm/60 sec. This wafer was prebaked in an oven at 80° C. for 30 minutes to obtain a coating film of 1.0 μm. Then, this coating film was subjected to exposure at various doses by means of a KrF excimer laser stepper (NA=0.35). After the exposure, the wafer was developed with a 2.38% tetramethylammonium hydroxide aqueous solution for 1 minute and then rinsed with water for 1 minute, whereupon the thickness of the remaining resist film was measured. Then, the remaining film thickness (standardized) was plotted against the dose for exposure (mj/cm$^2$), and the minimum dose (sensitivity) where the remaining film thickness became 0 was determined and found to be about 100 mj/cm$^2$. Thus, it was found to be a positive resist of high sensitivity. Then, a resist film obtained in the same manner as above was subjected to exposure (150 mj/cm$^2$) using a quartz mask, followed by development under the same condition as above, whereby a L & S pattern of 0.5 μm with an excellent profile was obtained.

EXAMPLE 8

The operation was conducted in the same manner as in Example 7 except that a compound having the following formula was used as the ammonium salt.

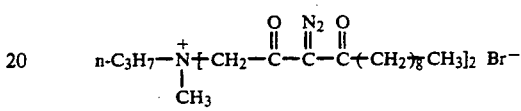

A sensitivity of 80 mj cm$^2$ was obtained, and pattern of 0.5 μm with an excellent profile was obtained.

EXAMPLE 9

The operation was conducted in the same manner as in Example 7 except that a compound having the following formula was used as the ammonium salt.

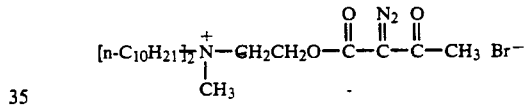

A sensitivity of 90 mj/cm$^2$ was obtained, and a L & S pattern of 0.5 μm with an excellent profile was obtained.

PREPARATION EXAMPLE 6

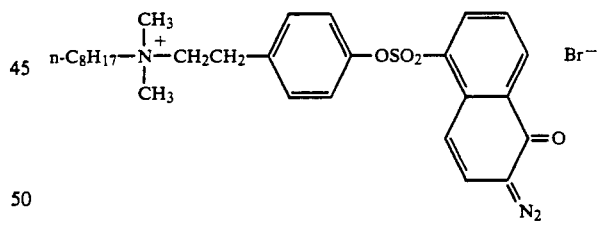

6.1 Preparation of

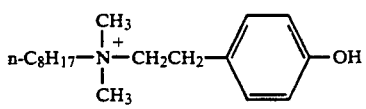

Into a 100 ml three-necked flask equipped with a reflux condenser, a dropping funnel and a stirrer, 10.0 g (50.0 mmol) of 4-(2-bromoethyl)phenol was introduced, and 8.65 g (55.0 mmol) of N,N-dimethyl-n-octylamine was dropwise added from the dropping funnel over a period of 5 minutes. After completion of the dropwise addition, the mixture was heated to 90° C. and stirred for 2 hours. After completion of the reaction, the reaction mixture was dissolved in 15 ml of ethanol, and the solution was poured into 300 ml of n-hexane. The separated viscous oil component was separated and dried to obtain the above identified compound.

Amount: 17.0 g, Yield: 95%.

¹H-NMR (CDCl₃) δ: 0.87 (3H,t,J=7.2 Hz), 1.10-1.48 (10H,m), 1.50-1.68 (2H,m), 2.76-2.94(2H,m), 3.21(6H,s), 3.37-3.63(5H,m), 6.95(2H,d,J=8.6 Hz), 7.02(2H,d,J=8.6 Hz).

MASS (m/e): 358 M(+).

6.2 Preparation of

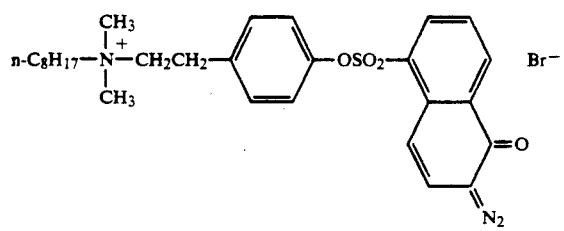

Into a 100 ml three-necked flask equipped with a reflux condenser, a dropping funnel and a stirrer, 7.74 g (21.6 mmol) of the compound obtained in step 6.1, 5.80 g (21.6 mmol) of 1,2-naphthoquinonediazido-5-sulfonic acid chloride, 60 ml of acetone and 20 ml of methanol were introduced. Then, 3.31 ml (23.7 mmol) of triethylamine was dropwise added thereto from the dropping funnel over a period of 10 minutes. After completion of the dropwise addition, the mixture was stirred at room temperature for 2 hours and concentrated under reduced pressure. The concentrated solution was poured into 300 ml of 1% hydrochloric acid. The separated oil component was collected and dried, and the obtained solid was recrystallized from ethanol to obtain the above identified compound.

Amount: 9.53 g, Yield: 75%.

¹H-NMR (CDCl₃) 0.85 (3H,t,J=7.2 Hz), 0.98-1.422 (10H,m), 1.53-1.71 (2H,m), 2.96-3.15 (2H,m), 3.33-3.54 (2H,m), 3.47 (6H,s), 3.64-3.90 (2H,m), 6.86 (2H,d,J=7.5 Hz), 7.24-7.39 (3H,m), 7.41-7.54 (2H,m), 8.10 (2H,d,J=7.6 Hz), 8.63 (2H,d,J=7.6 Hz).

IR (KBr): 2,150 cm⁻¹ (C=N₂).

Elemental Analysis (C₂₈H₃₆N₃O₄SBr)

C=57.03% (calculated: 56.95%)
H=6.20% (calculated: 6.14%)
N=7.02% (calculated: 7.11%)
S=5.49% (calculated: 5.43%)

PREPARATION EXAMPLE 7

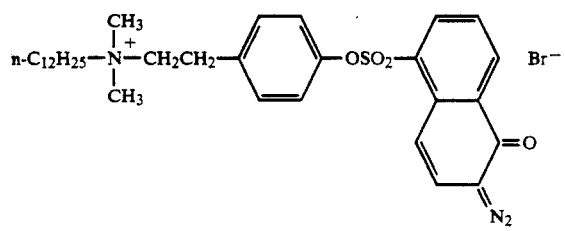

7.1 Preparation of

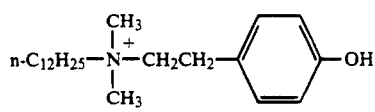

Into a 100 ml three-necked flask equipped with a reflux condenser, a dropping funnel and a stirrer, 10.0 g (50.0 mmol) of 4-(2-bromoethyl)phenol was introduced, and then 15.2 ml (55.0 mmol) of N,N-dimethyl-n-dodecylamine was dropwise added from the dropping funnel over a period of 5 minutes. After completion of the dropwise addition, the mixture was heated to 90° C. and stirred for 2 hours. After completion of the reaction, the reaction mixture was dissolved in 15 ml of ethanol. The solution was poured into 300 ml of n-hexane. The separated viscous oil component was collected and dried to obtain the above identified compound.

Amount: 18.6 g, Yield: 90%.

¹H-NMR (CDCl₃) δ: 0.85 (3H,t,J=7.5 Hz), 1.05-1.45 (18H,m), 1.50-1.75 (2H,m), 2.73-2.88 (2H,m), 3.15 (6H,s), 3.33-3.60 (5H,m), 6.87 (2H,d,J=8.6 Hz), 6.94 (2H,d,J=8.6 Hz).

MASS (m/e): 414 M(+).

7.2 Preparation of

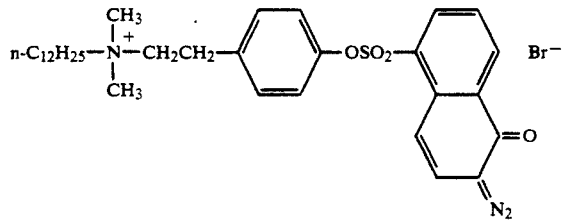

Into a 100 ml three-necked flask equipped with a reflux condenser, a dropping funnel and a stirrer, 6.40 g (16.4 mmol) of the compound obtained in step 7.1, 4.40 g (16.4 mmol) of 1,2-naphthoquinonediazido-5-sulfonic acid chloride, 60 ml of acetone and 20 ml of methanol were introduced, and 2.51 ml (18.0 mmol) of triethylamine was dropwise added thereto from the dropping funnel over a period of 10 minutes. After completion of the dropwise addition, the mixture was stirred at room temperature for hours and concentrated under reduced pressure. The concentrated solution was poured into 100 ml of 1% hydrochloric acid. The separated oil component was collected and dried. The obtained solid was recrystallized from ethanol to obtain the above identified compound. Amount: 6.94 g, Yield: 65%.

¹H-NMR (CDCl₃) δ: 0.84 (3H,t,J=7.0 Hz), 1.00-1.45 (18H,m), 1.55-1.75 (2H,m), 2.92-3.07 (2H,m), 3.30-3.52 (2H,m), 3.31 (6H, s), 3.60-3.85 (2H,m), 6.88 (2H,d,J=7.8 Hz), 7.22-7.36 (3H,m), 7.40-7.52 (2H,m), 8.12 (2H,d,J=7.8 Hz), 8.62 (2H,d,J=7.8 Hz).

IR (KBr): 2,150 cm⁻¹ (C=N₂).

Elemental Analysis (C₃₂H₄₄N₃O₄SBr)

C=59.10% (calculated: 59.43%)
H=6 52% (calculated: 6.86%)
N=6.17% (calculated: 6.50%)
S=5.33% (calculated: 5.00%)

PREPARATION EXAMPLE 8

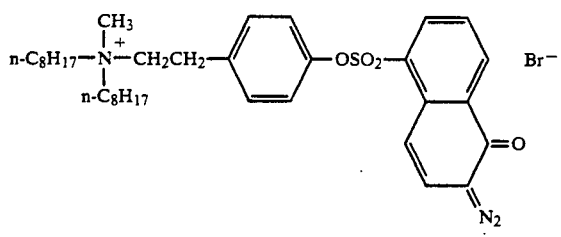

8.1 Preparation of

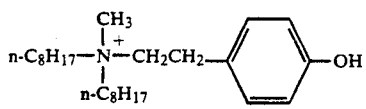

Into a 100 ml three-necked flask equipped with a reflux condenser, a dropping funnel and a stirrer, 10.0 g (50.0 mmol) of 4-(2-bromoethyl)phenol was introduced, and 14.0 g (55.0 mmol) of N,N-di-n-octylmethylamine was dropwise added from the dropping funnel over a period of 5 minutes. After completion of the dropwise addition, the mixture was heated at 90° C. and stirred for 3.5 hours. After completion of the reaction, the reaction mixture was dissolved in 15 ml of ethanol, and the solution was poured into 300 ml of n-hexane. The separated viscous oil component was collected and dried to obtain the above identified compound.

Amount 19.6 g, Yield: 86%.

$^1$H-NMR (CDCl$_3$) δ: 0.87 (6H,t,J=7.0 Hz), 1.00–1.72 (24H,m), 2.62–2.81 (4H,m), 3.02 (3H,s), 3.24–3.52 (4H,m), 3.82 (1H,bs), 6.83 (2H,d,J=8.5 Hz), 6.82 (2H,d,J=8.5 Hz).

MASS (m/e): 456 M(+).

8.2 Preparation of

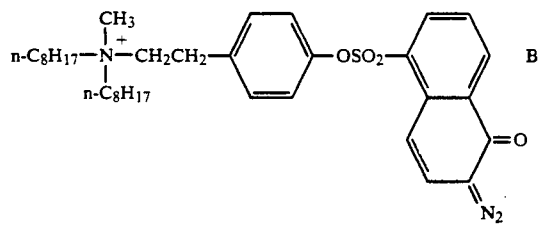

Into a 100 ml three-necked flask equipped with a reflux condenser, a dropping funnel and a stirrer, 8.03 g (17.6 mmol) of the compound obtained in step 8.1, 4.72 g (17.6 mmol) of 1,2-naphthoquinonediazido-5-sulfonic acid chloride, 60 ml of acetone and 20 ml of methanol were introduced. Then, 2.0 ml, 19.4 (mmol) of triethylamine was dropwise added thereto from the dropping funnel over a period of 10 minutes. After completion of the dropwise addition, the mixture was stirred at room temperature for 3 hours and concentrated under reduced pressure. The concentrated solution was poured into 300 ml of 1% hydrochloric acid. The separated oil component was collected and dried. The obtained solid was recrystallized from ethanol to obtain the above identified compound.

Amount: 5.12 g, Yield: 42%.

$^1$H-NMR (CDCl$_3$) δ: 0.86 (6H,t,J=7.2 Hz), 0.95–1.75 (24H,m), 2.75–2.90 (4H,m), 3.27–3.45 (2H,m), 3.24 (3H,s), 3.52–3.73 (2H,m), 6.85 (2H,d,J=8.0 Hz), 7.20–7.36 (3H,m), 7.41–7.55 (2H,m), 8.14 (2H,d,J=7.7 Hz), 8.63 (2H,d,J=7.7 Hz).

IR ( KBr) 2,150 cm$^{-1}$ (C=N$_2$).

Elemental Analysis: (C$_{35}$H$_{50}$N$_3$O$_4$SBr)

C=61.13% (calculated: 61.03%)
H=7.33% (calculated: 7.32%)
N=6.15% (calculated: 6.10%)
S=5.07% (calculated: 4.66%)

EXAMPLE 10

A resist composition having the following composition was prepared.

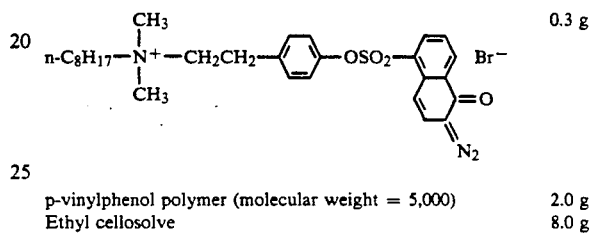 0.3 g p-vinylphenol polymer (molecular weight = 5,000)   2.0 g
Ethyl cellosolve   8.0 g This resist solution was spin-coated at a rate of 2,500 rpm/60 sec on a silicon wafer having hexamethyldisilazan (HMDS) spin-coated at thereon a rate of 2,000 rpm/60 sec. This wafer was prebaked in an oven at 80° C. for 30 minutes to obtain a coating film of 1.0 μm. Then, the coating film was subjected to exposure at various doses by means of i-line stepper (NA=0.40). After the exposure, the wafer was developed with a 2.38% tetramethylammonium hydroxide aqueous solution for 1 minute, and then rinsed with water for 1 minute, whereupon the thickness of the remaining resist film was measured. Then, the remaining film thickness (standardized) was plotted against the dose (mj/cm$^2$), and the minimum dose (sensitivity) where the remaining film thickness became 0 was determined and found to be about 200 mj/cm$^2$. Thus, it was found to be a positive resist of high sensitivity. Then, a resist film obtained in the same manner as above was subjected to exposure (240 mj/cm$^2$) by means of a quartz mask, followed by development under the same condition as above, whereby a L & S pattern of 0.6 μm with an excellent profile was obtained.

EXAMPLE 11

The operation was conducted in the same manner as in Example 10 except that a compound of the following formula was used as the ammonium salt:

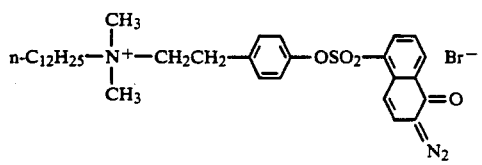

A sensitivity of 250 mj/cm$^2$ was obtained, and a L & S pattern of 0.6 μm with an excellent profile was obtained.

EXAMPLE 12

The operation was conducted in the same manner as in Example 10 except that a compound of the following structure was used as the ammonium salt:

n-C$_8$H$_{17}$—N$^+$(CH$_3$)(n-C$_8$H$_{17}$)—CH$_2$CH$_2$—C$_6$H$_4$—OSO$_2$—[naphthoquinone diazide] Br$^-$ A sensitivity of 270 mj/cm$^2$ was obtained, and a L & S pattern of 0.6 μm with an excellent profile was obtained.

EXAMPLE 13

The operation was conducted in the same manner as in Example 10 except that as the stepper, a KrF excimer laser stepper (NA=0.38) was used. As a result, a sensitivity of 400 mj/cm$^2$ was obtained, and a L & S pattern of 0.6 μm with an excellent profile was obtained.

PREPARATION EXAMPLE 9 o-NO$_2$-C$_6$H$_4$—CH$_2$—O—C(=O)—CH$_2$CH$_2$—N$^+$(CH$_3$)$_2$—n-C$_{12}$H$_{25}$  I$^-$

9.1 Preparation of o-NO$_2$-C$_6$H$_4$—CH$_2$—O—C(=O)—CH$_2$CH$_2$—I

Into a 100 ml three-necked flask equipped with a reflux condenser, a dropping funnel and a stirrer, 10 g (0.05 mol) of 3-iodopropionic acid and 40 ml of methanol were introduced and stirred. Then, a solution obtained by dissolving 2 g (0.05 mol) of sodium hydroxide in 20 ml of methanol, was dropwise added over a period of 30 minutes. As the dropwise addition proceeded, white precipitates formed. After completion of the dropwise addition, the mixture was stirred at 50° C. for 1 hour. After completion of the reaction, the solvent was distilled off under reduced pressure, and the residue was dried under vacuum.

Into a 300 ml three-necked flask equipped with a reflux condenser, a dropping funnel and a stirrer, a solution obtained by dissolving 5 g (0.0225 mol) of the above-mentioned sodium 3-iodopropionate in 80 ml of pure water and a solution obtained by dissolving 6.32 g (0.0293 mol) of o-nitrobenzyl bromide, were introduced, and the mixture was heated and refluxed for 4 hours under a nitrogen stream. After completion of the reaction, ethanol was distilled off under reduced pressure, and the residue was extracted twice with 50 ml of chloroform. The chloroform solution was dried and concentrated, and then the above identified compound was isolated by silica gel column chromatography.

Amount 5.65 g, Yield: 75%.

9.2 Preparation of o-NO$_2$-C$_6$H$_4$—CH$_2$—O—C(=O)—CH$_2$CH$_2$—N$^+$(CH$_3$)$_2$—n-C$_{12}$H$_{25}$  I$^-$ Into a 50 ml three-necked flask equipped with a reflux condenser, a dropping funnel and a stirrer, 2 g (9.36 mmol) of N,N-dimethyl-n-dodecylamine and 2 ml of dry ethanol were introduced and stirred. Then, a solution obtained by dissolving 3.76 g (11.2 mmol) of the compound obtained in step 9.1 in 10 ml of dry ethanol, was dropwise added over a period of 30 minutes, and then the mixture was heated and refluxed for 2 hours. After completion of the reaction, the reaction mixture was poured into 100 ml of ethyl ether. The precipitates formed were separated, then washed with 5 ml of ethyl ether and dried under vacuum to obtain the above identified compound.

Amount: 2.82 g, Yield: 55%.

Characteristic peaks in the $^1$H-NMR spectrum (CDCl$_3$):

A (δ 0.86 terminal methyl of a long chain alkyl group)
B (δ 3.25 —N$^+$—(CH$_3$)$_2$)
C (δ 7.3–8.3 aromatic hydrogen)

PREPARATION EXAMPLE 10 o-NO$_2$-C$_6$H$_4$—CH$_2$—O—C(=O)—CH$_2$CH$_2$—N$^+$(CH$_3$)(n-C$_8$H$_{17}$)$_2$  I$^-$

The operation was conducted in the same manner as in Preparation Example 9 except that 2.4 g of N-methyl-di-n-octylamine was used instead of 2 g of N,N-dimethyl-n-dodecylamine in step 9.2 in Preparation Example 9.

Amount: 2.76 g, Yield: 50%.

PREPARATION EXAMPLE 11 o-NO$_2$-C$_6$H$_4$—CH$_2$—O—C(=O)—C$_6$H$_4$—CH$_2$—N$^+$(CH$_3$)$_2$—n-C$_{12}$H$_{25}$  I$^-$

The operation was conducted in the same manner as in Preparation Example 9 except that 13 g of 4-iodomethylbenzoic acid was used instead of 10 g of 3-iodopropionic acid in step 9.1 in Preparation Example 9.

Amount: 3.42 g, Yield: 60%.

EXAMPLE 14

A resist composition having the following formula was prepared.

o-NO$_2$-C$_6$H$_4$—CH$_2$—O—C(=O)—CH$_2$CH$_2$—N$^+$(CH$_3$)$_2$—n-C$_{12}$H$_{25}$  I$^-$

| p-vinylphenyl polymer (molecular weight = 5,000) | 2.0 g |
|---|---|
| Ethyl cellosolve | 8.0 g |

This resist solution was spin-coated at a rate of 2,500 rpm/60 sec on a silicon wafer having hexamethyldisilazane (HMDS) spin-coated thereon at a rate of 2,000 rpm/60 sec. This wafer was prebaked in an oven at 80° C. for 30 minutes to obtain a coating film of 1.0 μm. Then, the coating film was subjected to exposure at various doses by means of a KrF excimer laser stepper (NA=0.35). After the exposure, the wafer was developed with a 2.38% tetramethylammonium hydroxide aqueous solution for 1 minute, and then rinsed with water for 1 minute, whereupon the thickness of the remaining resist film was measured. Then, the remaining remaining resist film was measured. Then, the remaining film thickness (standardized) was plotted against the dose for exposure (mj/cm²), and the minimum dose (sensitivity) where the remaining film thickness became 0, was determined and found to be about 100 mj/cm². Thus, it was found to be a positive resist having a high sensitivity.

Then, a resist film prepared in the same manner as mentioned above was subjected to exposure (150 mj/cm²) using a quartz mask, followed by development under the same conditions as above, whereby a L & S pattern of 0.5 μm with an excellent profile was obtained.

EXAMPLE 15

The operation was conducted in the same manner as in Example 14 except that 0.25 g of a compound of the following structure was used as the ammonium salt:

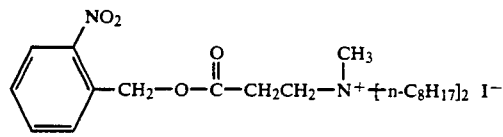

A sensitivity of 80 mm/cm² was obtained, and a L & S pattern of 0.5 μm with an excellent profile was obtained.

EXAMPLE 16

The operation was conducted in the same manner as in Example 14 except that a compound having the following formula was used as the ammonium salt:

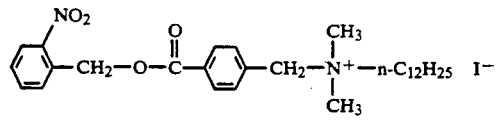

A sensitivity of 90 mj cm² was obtained, and a L & S pattern of 0.5 μm with an excellent profile was obtained.

As described in the foregoing, the positive photoresist composition of the present invention has high transparency after exposure in a ultraviolet or far ultraviolet region, whereby the sensitivity and the resolution can be improved. Further, the solubilization-inhibiting ability of the solubilization-inhibitor is high, and the film remaining rate at the non-exposed portion is high, and it is thereby possible to form a resist pattern with high precision. Further, it has sensitivity to e.g. electron beams, whereby a pattern similar to that formed by ultraviolet rays or far ultraviolet rays, can be formed. Thus, such a composition can be used as a resist for the production of LSI or super LSI for which the requirements for resolution are expected to be more severe from now on.

We claim:

1. A positive resist composition comprising, as the main components:
    (A) an aromatic group-containing alkali-soluble resin AND
    (B) a compound having an ammonium salt skeleton which is acid decomposable and which contains an acid-forming agent which generates an acid when irradiated with active radiation; AND
    (1) wherein the said ammonium salt is represented by the following formula (I),

wherein each of $R_1$ and $R_2$ which may be the same or different, is a chain alkyl group having from 1 to 30 carbon atoms, a polycyclic alkyl group, a chain alkoxy group, a polycyclic alkoxy group or an allyl group, $R_3$ is a chain alkyl group having from 1 to 30 carbon atoms, a polycyclic alkyl group or an allyl group, $X^-$ is a halogen, $HSO_4^-$, $ClO_4^-$ or $BF_4^-$, $Y_1$ is an acid-decomposable ester, carbonate, silyl ether or silyl ester group, m is an integer of at least 1 and n is an integer inclusive of 0, provided that $m+n=4$, OR
    (2) wherein the said ammonium salt is represented by the following formula (II),

wherein each of $R_4$ and $R_5$ which may be the same or different, is a chain alkyl group having from 1 to 30 carbon atoms, a polycyclic alkyl group, a chain alkoxy group, a polycyclic alkoxy group or an allyl group, $R_6$ is a hydrogen atom, a chain alkyl group having rom 1 to 30 carbon atoms, a polycyclic alkyl group or an allyl group, $X^-$ is a halogen, $HSO_4^-$, $ClO_4^-$ or $BF_4^-$, $Y_2$ is a radiation-decomposable group of the formula:

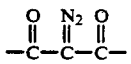

m is an integer of at least 1, and n is an integer inclusive of 0, provided that $m+n=4$, OR
    (3) wherein said ammonium salt is represented by the following formula (III),

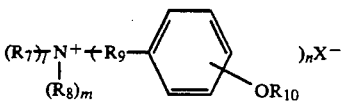

wherein each of $R_7$, $R_8$ and $R_9$ which may be the same or different, is a chain alkyl group having from 1 to 3 carbon atoms, a polycyclic alkyl group, a chain alkoxy group, a polycyclic alkoxy group or an allyl group, $R_{10}$ is:

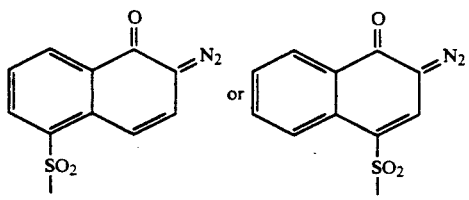

$X^-$ is a halogen, $HSO_4^-$, $ClO_4^-$ or $BF_4^-$, each of l and m is an integer inclusive of 0, and n is an integer of at least 1, provided that $l+m+n=4$, OR (4) wherein ammonium salt is represented by the following formula (IV),

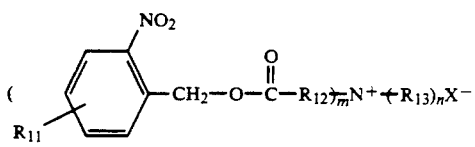

wherein $R_{11}$ is a hydrogen atom, a chain alkyl group having from 1 to 30 carbon atoms, a polycyclic alkyl group or a nitro group, $R_{12}$ is a chain alkyl group having from 1 to 30 carbon atoms, a polycyclic alkyl group or an allyl group, $R_{13}$ is a chain alkyl group having from 1 to 30 carbon atoms, a polycyclic alkyl group or an allyl group, $X^-$ is a halogen, $HSO_4^-$, $ClO_4^-$ or $BF_4^-$, m is an integer of at least 1, and n is an integer inclusive of 0, provided that $m+n=4$.

2. The positive resist composition according to claim 1, wherein the compound having an ammonium salt as skeleton, is decomposable by an acid.

3. The positive resist composition according to claim 1, wherein the compound having an ammonia salt as skeleton, is decomposable by active radiation.

4. The positive resist composition according to claim 1 or 2, wherein the compound having an ammonium salt as skeleton, is a compound containing at least one alkyl group having an acid-decomposable group and which contains an acid-forming agent which generates an acid when irradiated with active radiation, and wherein said ammonium salt has a structure represented by the following formula (1), $$(R_1-Y_1-R_2)_m N^+ (R_3)_n X^- \quad (1)$$

wherein each of $R_1$ and $R_2$ which may be the same or different, is a chain alkyl group having from 1 to 30 carbon atoms, a polycyclic alkyl group or an allyl group, $X^-$ is a halogen, $HSO_4^-$, $ClO_4^-$, or $BF_4^-$, $Y_1$ is an acid-decomposable ester, carbonate, silyl ether or silyl ester group, m is an integer of at least 1 and n is an integer inclusive of 0, provided that $m+n=4$.

5. The positive resist composition according to claim 1 or 3, wherein the compound having an ammonium salt as skeleton, has a structure of the following formula (2):

$$[R_4-Y_2-R_5]_m N^+ (R_6)_n X^- \quad (2)$$

wherein each of $R_4$ and $R_5$ which may be the same or different, is a chain alkyl group having from 1 to 30 carbon atoms, a polycyclic alkyl group, a chain alkoxy group, a polycyclic alkoxy group or an allyl group, $R_6$ is a hydrogen atom, a chain alkyl group having from 1 to 30 carbon atoms, a polycyclic alkyl group or an allyl group, $X^-$ is a halogen$^-$, $HSO_4^-$, $ClO_4^-$ or $BF_4^-$, $Y_2$ is a radiation-decomposable group of the formula:

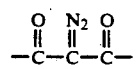

m is an integer of at least 1, and n is an integer inclusive of 0, provided that $m+n=4$.

6. The positive resist composition according to claim 1 or 3, wherein the compound having an ammonium salt as skeleton, has a structure of the following formula (3):

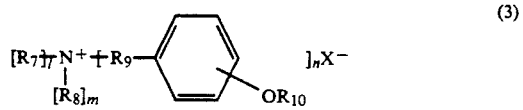

wherein each of $R_7$, $R_8$ and $R_9$ which may be the same or different, is a chain alkyl group having from 1 to 30 carbon atoms, a polycyclic alkyl group, a chain alkoxy group, a polycyclic alkoxy group or an allyl group, $R_{10}$ is

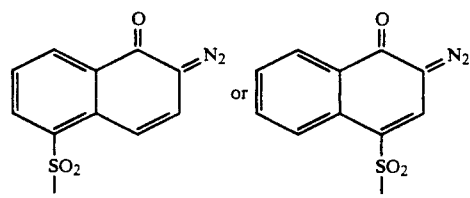

$X^-$ is a halogen$^-$, $HSO_4^-$, $ClO_4^-$ or $BF_6^-$, each of l and m is an integer inclusive of 0, and n is an integer of at least 1, provided that $l+m+n=4$.

7. The positive resist composition according to claim 1 or 3, wherein the compound having an ammonium salt as skeleton, has a structure of the following formula (4):

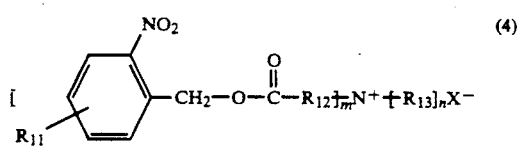

wherein $R_{11}$ is a hydrogen atom, a chain alkyl group having from 1 to 30 carbon atoms, a polycyclic alkyl group or a nitro group, $R_{12}$ is a chain alkyl group having from 1 to 30 carbon atoms, a polycyclic alkyl group or an allyl group, $R_{13}$ is a chain alkyl group having from 1 to carbon atoms, a polycyclic alkyl group or an allyl group, $X^-$ is a halogen$^-$, $HSO_4^-$, $ClO_4^-$ or $BF_6^-$, m is an integer of at least 1, and n is an integer inclusive of 0, provided that $m+n=4$.

* * * * *